United States Patent [19]

Treves et al.

[11] Patent Number: 4,729,380

[45] Date of Patent: Mar. 8, 1988

[54] IRIDIUM 191-M GENERATOR

[75] Inventors: Salvador Treves, Newton; Chris C. Cheng, Brookline, both of Mass.

[73] Assignee: The Children's Medical Center Corporation, Boston, Mass.

[21] Appl. No.: 492,336

[22] Filed: May 6, 1983

Related U.S. Application Data

[63] Continuation of Ser. No. 290,683, Aug. 6, 1981, abandoned.

[51] Int. Cl.[4] ................................................ A61B 5/05

[52] U.S. Cl. .................................... 128/659; 128/653; 128/654; 423/2; 250/432 PD

[58] Field of Search .................. 252/1, 625, 644, 645; 424/1, 1.5; 210/633, 634, 638, 660, 679, 682; 423/249, 2, 22, 593; 128/659, 653

[56] References Cited

PUBLICATIONS

Yano et al., (1968), J. Nucl. Med. 9, 1.

Treves et al., (1976), Circulation 54(1), 275.

Hnatowich et al., (1977), Radiology 123, 189.

Bailar et al., (1973), *Comprehensive Inorganic Chemistry* 3, 1230–1231.

Gmelins, Gmelins Handbook Der Anorganischen Chemie, (1949), 05–66, 67.

Sidgwick, The Chemical Elements and Their Compounds, (1950), II, 1499–1500.

*Primary Examiner*—John F. Terapane

*Assistant Examiner*—T. J. Wallen

[57] ABSTRACT

Potassium osmate, of the formula $K_2 Os O_2 (OH)_4$), used to make a column for the generation of Ir-191 m, which is used in first pass angiography to detect cardiac defects in patients.

3 Claims, 2 Drawing Figures

IRIDIUM 191-M GENERATOR

BACKGROUND OF THE INVENTION

This invention was made with government funds on a grant awarded by the Department of Energy (DE-ACO2-82ER60084) and on a grant awarded by the National Institutes of Health. The government has certain rights in this invention.

This application is a continuation of application Ser. No. 290,683, filed 8/6/81 now abandoned.

This invention relates to iridium-191 m (Ir-191 m), which is used in angiography.

Ir-191 m is useful for angiography because it has a short half-life (4.96 sec.) and useful photon-energy radiation. Yano et al. (1968) J. Nucl. Med. 9, 1; Treves et al. (1976) Circulation 54(1), 275; and Hnatowich et al. (1977) Radiology 123, 189 describe the production of Ir-191 m, for use in a continous infusion procedure, from the Osmium-191 (Os-191)-containing salt hexachloro-osmate ($K_2(O_sCl_6)$). Just prior to infusion, the hexachloro-osmate is loaded onto a resin column and Ir-191 m is then eluted with NaCl solution.

SUMMARY OF THE INVENTION

In general, the invention features potassium osmate, of the formula $K_2(Os\ O_2(OH_4))$, which is used to make a column for the generation of Ir-191 m, which is used in first pass angiography to detect cardiac defects in patients. The method involves positionihg a gamma scintillation camera over the patient's chest, inserting a needle into a blood vessel of the patient, the needle being operatively connected to an eluate injector, which is connected to and positioned downstream from a generator column containing a resin loaded with a solution comprising a mixture of $K_2(Os\ O_2(OH)_2\ Cl_2$ and $K_2(Os\ O_2\ Cl_4)$, which generator column is connected to and positioned downstream from an eluant injector, placing an eluant in said eluant injector, the eluant being capable of eluting Ir -191 m from the generator column, injecting the eluant into the generator column to elute Ir-191 m therefrom and into the eluate injector, injecting the eluate into a patient via the needle, and detecting Ir-191 m, using the gamma scintillation camera, in the patient's chest to detect any cardiac defects therein.

In another aspect, the invention features a method of making potassium osmate involving mixing Os-191 with KOH and $KNO_3$ to form a mixture, fusing the mixture to form potassium perosmate, and reducing the potassium perosmate to yield potassium osmate. Preferably, the ratio, by weight, of mixed reagents is about 1 Os-191:4 KOH:4 $KNO_3$, and reducing is carried out using ethanol.

In another aspect, the invention features a solution containing a mixture of $K_2(Os\ O_2(OH)_2Cl_2)$ and $K_2(Os\ O_2\ Cl_4)$.

In still another aspect, the invention features a method for generating Ir-191 m including dissolving potassium osmate in HCl, loading the resultant solution, in a column, onto a resin capable of absorbing it, and eluting Ir-191 m from the column using an eluant capable of eluting Ir-191 m. Preferably the eluant has a pH of about 1.

In yet another aspect the invention features apparatus for generating Ir-191 m including a generator column containing a resin loaded with a solution containing a mixture of $K_2(Os\ O_2(OH)_2\ Cl_2)$ and $K_2(Os\ O_2\ Cl_4)$.

The methods and apparatus of the invention allow first-pass angiography to be performed on patients with minimal interfering background radiation, and with minimal exposure to toxic osmium.

Other advantages and features of the invention will be apparent from the following description of the preferred embodiment thereof, and from the claims.

DESCRIPTION OF THE PREFERRED EMBODIMENT

We turn now to the description of the preferred embodiment, first briefly describing the drawings thereof.

Drawings

Potassium Osmate

The method described herein for making potassium osmate and using it to generate Ir-191 m are described in Cheng et al. (1980) J. Nucl. Med. 21, 1169.

The first step in making potassium osmate involves sealing 20 mg of powdered, enriched osmium-190 metal in a small quartz ampule and irradiating it for 20 hours at a neutron flux of $5.5\times10^{14}$ neutrons/cm$^2$-sec. This produces about 800 mCi of Os-191, which has a half-life ($T_{\frac{1}{2}}$) of 15.4 days, and is highly toxic. By-product osmium isotopes produced in this reaction have a much shorter half-life than Os-191, and are present in negligible amounts by the time the material is ready for use in angiography.

Figure 1:
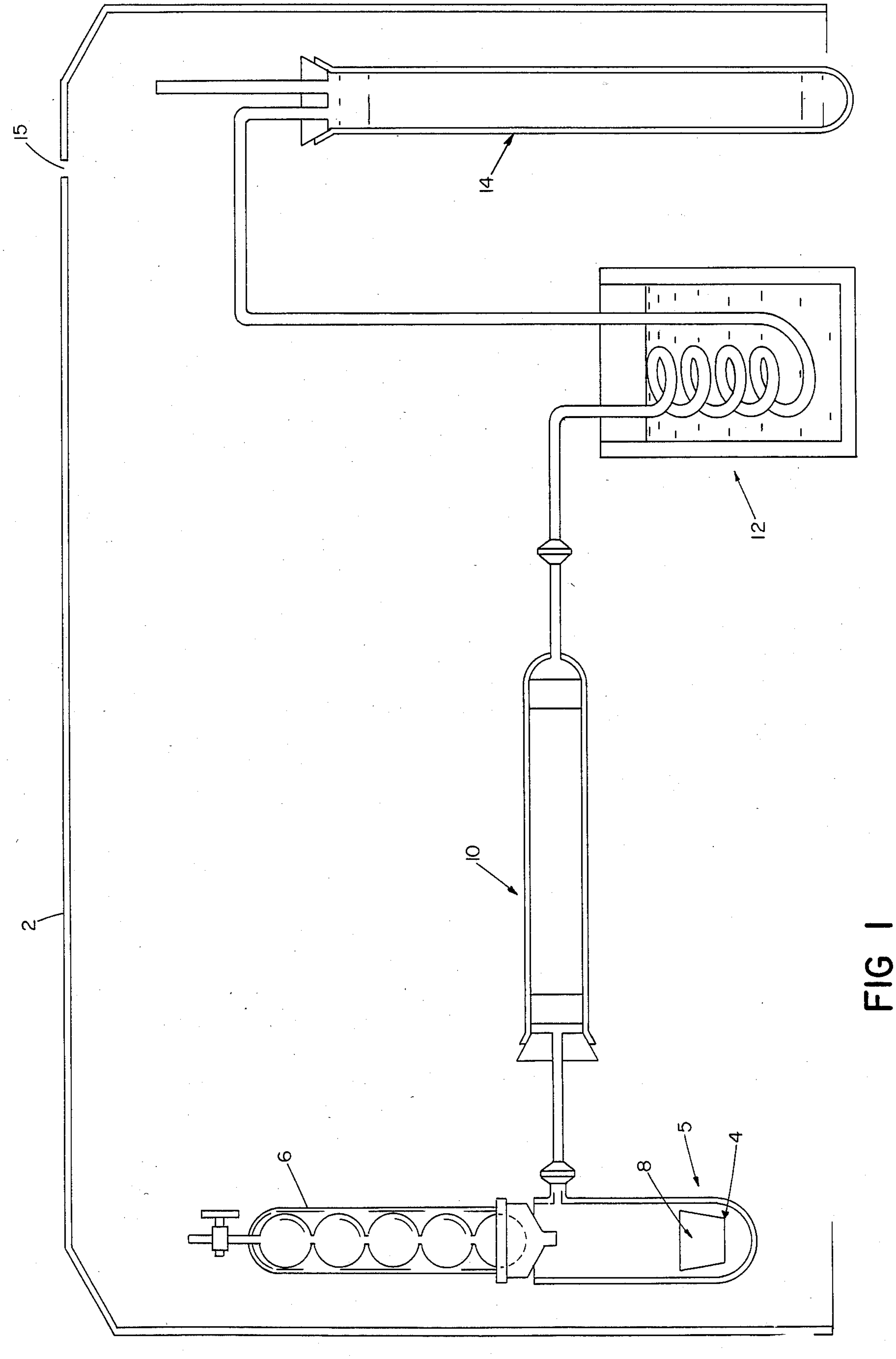
FIG. 1 is a diagrammatic representation of apparatus for fusing Os-191.

The second and third steps of the process are carried out in the closed system shown in FIG. 1. The mixing and fusing apparatus is enclosed within lead-shielded hood 2. Twenty mg of enriched Os-191 are mixed together with 80 mg KOH and 80 mg $KNO_3$ in zirconium crucible 4, placed in the bottom of test tube 5, which is equipped with condensor 6. The resultant mixture 8 is then fused at 350° C.-500° C. for 2 hrs. Any volatile Osmium compound produced in the process passes through filter 10, containing activated charcoal and glass wool, through cold trap 12, and finally through 1 inch-diameter charcoal filter 14 before passing into hood 2. A pump (not shown) pumps air from hood ventilation duct 15 through charcoal filter paper to monitor Os-191 escaping into the air; generally less than 1 $\mu$Ci of Os-191 escapes as a result of processing an 800-mCi sample.

The fusion process produces a red cake of potassium perosmate, $K_2(OsO_4(OH)_2)$, which is then dissolved in sterile water. This solution is mixed with absolute ethanol, which reduces the potassium perosmate to potassium osmate, $K_2(Os\ O_2(OH)_4)$, which is recovered as a pure, hydrated purple precipitate.

Ir-191 m Generator

Figure 2:
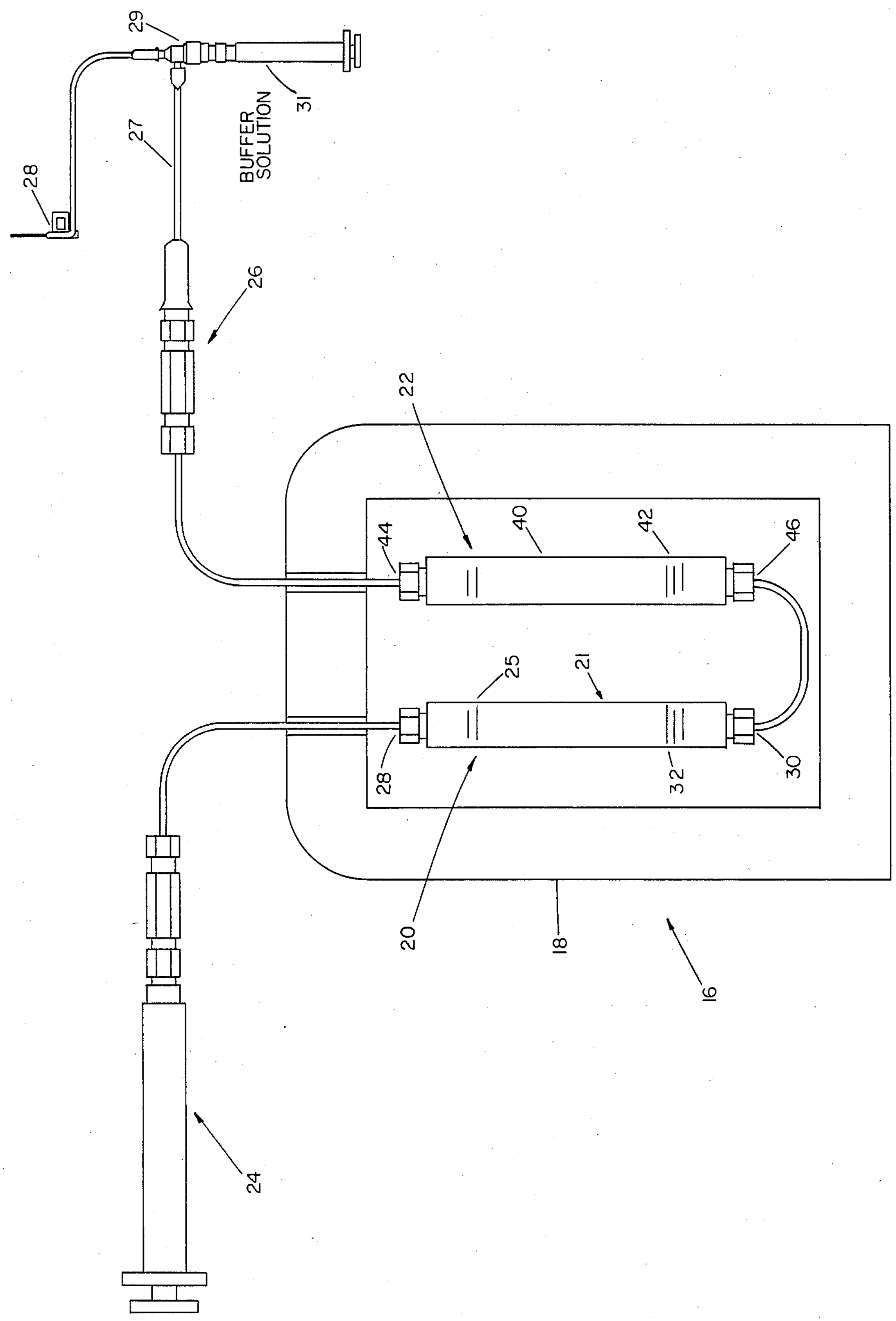
FIG. 2 is a diagrammatic representation of apparatus for generating Ir-191 m.

There is shown in FIG. 2 Ir-191 m generator 16, which includes lead container 18, enclosing main generator column 20, scavenger column 22, eluant injector 24, and Ir-191 m injector 26, fitted with needle 27. The components are all sterilized and assembled under sterile conditions.

Main generator column 20 includes 5 cm long polymethylmethacrylate (Plexiglass) tube 21, of 1.25 cm o.d. and 4.4 m m i. d, and a total capacity of 0.9 ml.

One gram of strongly basic, macroporous anion exchange resin in chloride form (Bio-Rad AGMP-1) in 100–200 mesh size is washed first with distilled water and then with 0.1 N HCl. The resin is then placed in tube 21, and Teflon washers (not shown) and glass wool 32 are placed at both ends of the tube, which is then fitted at both ends with high pressure liquid chromatography fittings 28 and 30.

Scavenger column 22, whose function is to prevent the migration of toxic osmium-absorbed resin out of the generator, includes Lucite tube 40, of the same dimensions as tube 21. Column 22 is prepared by first washing one gram of Dowex-2X10 resin, in chloride form, with distilled water and then with 0.1 N HCl. Ten mg of newly purified pyrocatechol are dissolved in 20 ml of normal saline, pH 1, to produce a solution in which the washed resin is soaked, prior to being placed in tube 40 and then washed with 20 ml of normal saline, pH 1. Teflon washers (not shown) and glass wool 42 are placed in tube 40, the ends of which are fitted with high pressure liquid chromatography fittings 44 and 46.

Columns 20 and 22 are washed with 20 ml of normal saline, pH 1, prior to final assembly. In the final step in the preparation of the generator, potassium osmate is dissolved in 4 N HCl to produce a dark brown solution containing a mixture of $K_2(Os\ O_2(OH)_2Cl_2)$ and $K_2(Os\ O_2\ Cl_4)$. This solution is loaded onto the resin of generator column 20.

The generator remains stable and produces acceptable yields for at least one month, although the generator may form undesirable osmium species in as little as one day. Such undesirable species can be eliminated by passing 1–2 ml of eluant through the generator just prior to clinical use.

Angiography

The use, described herein, of the Ir-191 m generator in first-pass angiography is described in Treves et al. J. Nucl. Med. 21, 1151.

Prior to generating Ir-191 m, a patient in whom cardiac defects, e.g., left-to-right shunting, are to be detected, is placed in the supine position with a gamma scintillation camera, fitted with a collimator designed for low energies, positioned above the chest. Prior to use, a small amount of Os-191 is used to calibrate the camera; because Os-191 does not itself emit photons, the only photopeaks detected are from Ir-191 m. Two 20% windows in the dual pulse-height analyzer are set over the 65- and 129 -keV peaks.

Twenty-one or 23-gauge "butterfly" needle 28 (FIG. 2), connected to injector needle 27 by means of a conventional "T" connector 29, is inserted into an appropriate vein (e.g., wrist, arm, or jugular). Eluant injector 24 is charged with the volume of 0.9% NaCl, pH 1, necessary to elute the desired dosage of Ir-191 m; this volume varies with characteristics, e.g., age and weight, of the patient, and with activity per ml of the resin in the generator column, and is generally between 0.6 and 1 ml, to administer an Ir-191 m dose between about 24 m Ci and 80 m Ci. Ir-191 m dosage can also be increased by increasing the salinity of the eluant, but this can undesirably raise the osmolarity of the eluate.

The eluant in injector 24 is then injected into generator 20. Elution of Ir-191 m through the columns and into the patient, through one branch of the "T", occurs less than 2 sec. after eluant injection. The eluate contains 7–10% Ir-191 m and only 0.003–0.008% toxic Os-191. The eluate is sterile and free of pyrogens.

The eluate, as it leaves injector needle 27, is diluted with 1–10 ml of buffer solution, which enters the needle via the other branch 31 of the "T". The buffer solution is 25% 0.05 M $Na_2HPO_4$, pH 8.4, and 75% normal saline.

Angiography with the apparatus described herein produces true maximum count rates at about 150,000 cps. This counting rate results in significant count loss due to system dead time. The loss is measured using a small shielded source of Os-191 placed near the edge in the field of view of the gamma camera while the radioangiogram is carried out. As the count rate to the rest of the field increases beyond the linear response of the system, the apparent count rate of the small source decreases.

Correction for count losses is carried out in the following way. An average value (A) of the counts from the point source before deadtime occurs is calculated. A correction factor (CF) is calculated for each frame of the study using the formula: $CF=A/RC$, where RC is the recorded count rate of the point source in that frame. The corrected counts are obtained by multiplying the number of counts in the region of interest by the correction factor. The correction factor is $\exp(T-T_0)\ \ln 2/T_{\frac{1}{2}}$, where exp is the exponential function, T is the time (sec) from the beginning of the study, $T_0$ is the time (sec) at which the activity first appears, and $T_{\frac{1}{2}}$ is the physical half-life of Ir-191 m (4.96 sec).

Observed time-activity curves are corrected for the shape of the input bolus using deconvolution analysis. This is performed by the method of discrete Fourier transforms described in Williams (1977) J. Nucl. Med. 20, 568, and the resulting curves are filtered using a low-pass digital filter to remove high-frequency components. The pulmonary-to-systemic flow ratio (Qp:Qs) is determined by analysis of pulmonary dilution curves using the method described in Rabinovitch et al. (1977) Am. J. Cardiol. 39, 309.

The high Ir-191 m concentration of the eluate permits first pass, or serial, injections, rather than continuous infusion. This method minimizes interfering background radiation, and also exposes the patient to a minimal concentration of toxic osmium.

Kit

The angiography apparatus shown in FIG. 2 can be supplied in the form of a transportable kit, which includes the lead container and the two columns and their associated injectors, tubing, and reagents. The generator column is preferably supplied already containing an appropriate resin loaded with chlorinated potassium osmate.

OTHER EMBODIMENTS

Other embodiments are within the following claims. For example, the apparatus, resins, and reagents used in conjunction with the potassium osmate can be of a variety of configurations and compositions, so long as they produce a non-toxic Ir-191 m eluate suitable for angiography. A scavenger column, for example, might not be necessary where an acceptable toxicity level can otherwise be achieved. Also, the only essential component of the kit is the generator column, the remainder of the components being conventional apparatus likely already to be on hand in a large hospital.

We claim:

1. An apparatus for generating Iridium-191 comprising a generator column containing a resin loaded with a solution comprising a mixture of $K_2(OsO_2(OH)_2Cl_2)$ and $K_2(OsO_2Cl_4)$, an eluant injector, positioned upstream from said generator column, a scavenger column connected to and positioned downstream from said generator column, an eluate injector, including a needle for insertion into a blood vessel of a human patient, positioned downstream from said scavenger column, and a lead container enclosing said generator and scavenger columns.

2. Apparatus for generating iridium-191 m to be administered to a human, said apparatus comprising an eluate injector comprising:

(a) a generator column containing a resin loaded with the solution comprising a mixture of $K_2(OsO_2(OH)_2Cl_2)$ and $K_2(OsO_2Cl_4)$, and (b) means for administering iridium-191 m eluate generated from said column to said human.

3. A method of generating iridium-191 m comprising:

(a) providing an apparatus comprising an eluate injector, said injector comprising:

(1) a generator column containing a resin, and (2) means for administering iridium-191 m eluate generated from said column to a human;

(b) providing potassium osmate;

(c) dissolving said potassium osmate in HCl to form a solution comprising a mixture of $K_2(OsO_2(OH)_2Cl_2)$ and $K_2(OsO_2Cl_4)$;

(d) loading said solution onto said generator column; and (e) eluting iridium-191 m from said generator column using an eluant capable of eluting iridium-191 m.

* * * * *